(12) United States Patent
Brojek

(10) Patent No.: US 11,883,320 B2
(45) Date of Patent: Jan. 30, 2024

(54) METHOD OF PREPARING CRYOGENIC AIR

(71) Applicant: METRUM CRYOFLEX SP. Z O.O. SPÓŁKA KOMANDYTOWA, Stare Babice (PL)

(72) Inventor: Wiesław Brojek, Stare Babice (PL)

(73) Assignee: METRUM CRYOFLEX SP. Z O.O., SPOLKA KOMANDYTOWA, Stare Babice (PL)

(*) Notice: Subject to any disclaimer, the term of this patent is extended or adjusted under 35 U.S.C. 154(b) by 180 days.

(21) Appl. No.: 17/062,515

(22) Filed: Oct. 2, 2020

(65) Prior Publication Data

US 2021/0100683 A1  Apr. 8, 2021

Related U.S. Application Data

(60) Provisional application No. 62/909,751, filed on Oct. 2, 2019.

(51) Int. Cl.
*A61F 7/00* (2006.01)

(52) U.S. Cl.
CPC .......... *A61F 7/0085* (2013.01); *A61F 7/0053* (2013.01); *A61F 2007/006* (2013.01); *A61F 2007/0064* (2013.01)

(58) Field of Classification Search
CPC .......... A61B 18/0218; A61F 2007/006; A61F 2007/0064; A61F 7/0053; A61F 7/0085
See application file for complete search history.

(56) References Cited

U.S. PATENT DOCUMENTS

| | | | | |
|---|---|---|---|---|
| 4,880,003 A | * | 11/1989 | Donnerhack | A61F 7/0053 607/83 |
| 2002/0096174 A1 | * | 7/2002 | Hill | A61M 16/10 128/204.22 |

FOREIGN PATENT DOCUMENTS

SK          50512007 A3  * 12/2008

OTHER PUBLICATIONS

English Translation of Brojek (50512008), Method And Device For Cryogenic Therapy Applied On The Whole Body Of The Patient, 2008.*

* cited by examiner

*Primary Examiner* — Tigist S Demie
(74) *Attorney, Agent, or Firm* — Andrzej Malarz, Esq.

(57) ABSTRACT

A method of preparing cryogenic air for use in cryotherapy procedures, using liquid nitrogen and gaseous oxygen, characterized in that liquid nitrogen (1) is fed from a cryogenic nitrogen tank (2) via a cryogenic duct (3) to a reactor (4), wherein simultaneously a gas (7) containing oxygen in a concentration from 20% to 100% is fed from an oxygen source (5) to the reactor (4), through a gas duct (6), then, in the reactor (4), the liquid nitrogen (1) is evaporated using the gas (7) and both these components are mixed together, forming a cold breathable mixture (8), cooled to a set temperature of minus 80° C. to minus 160° C., which is further fed through a cold duct (9) terminated with an outlet (10) to a cryochamber (11).

7 Claims, 5 Drawing Sheets

METHOD OF PREPARING CRYOGENIC AIR

This application claims the priority of U.S. Provisional Patent Application No. 62/909,751, filed Oct. 2, 2019. The contents of U.S. Provisional Patent Application 62/909,751 are hereby incorporated by reference for all purposes.

FIELD OF THE INVENTION

This disclosure relates to a method of preparing cryogenic air for use in cryotherapy procedures.

BACKGROUND

The use of cryotherapy procedures employing the stimulus effect of low temperatures in the range of minus 80° C. to minus 160° C. acting over a short period of time is aimed at causing physiological and systematic reaction to cold stimuli. Such action supports the treatment of diseases particularly associated with human mobility limitations, such as inflammatory and degenerative joint diseases, rheumatoid arthritis (RA), ankylosing spondylitis (AS), shoulder impingement syndrome (SIS), spinal pain syndromes (surgically and conservatively treated), and, in addition, osteoporosis, fibromyalgia, connective tissue diseases, migraines and others.

Cryotherapy procedures allow for, among others, analgesic, anti-edematous, and anti-inflammatory effects, muscle tone reduction, strengthening and stimulation of the immune system, improvement of peristalsis peripheral vessels, cleansing and regeneration of the skin—anti-cellulite treatment, improvement of regeneration and healing processes, improvement of mood and increase of body efficiency.

In medical technology, devices for cryotherapy procedures are known, which consist of a low-temperature chamber, a system supplying such chamber with gas at cryogenic temperature, and systems controlling the operation of these devices.

For example, the device according to Polish patent specification PL 157168 includes: an air compressor, a dryer for removing steam from the compressed air, a heat exchanger and a container for liquefied gas, preferably liquid nitrogen. All these basic components of the device are connected to each other by tubing. The liquefied gas from the tank flows to the heat exchanger, where it cools the air to the cryogenic temperature, air then flows through an insulated line to the low-temperature chamber. The whole device is equipped with measurement, control and safety elements, and parts of this device containing agents at cryogenic temperature are equipped with thermal insulation.

A device for obtaining air at cryogenic temperature, intended for supplying a cryotherapy treatment chamber, comprising an air compressor, a dryer for removing steam from the compressed air, a heat exchanger and a container of liquefied gas is disclosed in German patent specification DE 3213919. The device is equipped with measurement, control and safety elements. Parts of the device containing agents at cryogenic temperature are provided with thermal insulation. The device requires a long start-up and preparation time.

A method of preparing cryogenic air fed to the cryogenic chamber and a device for implementing such method described in Polish patent specification PL 190 389 is known. This method involves compressing, drying and cooling the air. This method is characterized by the fact that the air is compressed to 1 Mpa in the compressor, dried in the adsorber and directed to purge the cryogenic purifiers. Then the system is blown through and the air guiding valves are closed. The next step is to open the valves at the liquid nitrogen tank, allowing liquid nitrogen to flow from the tank intended for cooling the cryogenic purifier into which the air compressed in the compressor and purified in the adsorption dryer is directed. Simultaneously with cooling the cryogenic purifier, a second cryogenic purifier is also cooled. When the temperature of the air flowing from the cryogenic purifier to the cryochamber increases to about minus 100° C., the cryogenic purifier closes automatically and the air is sent to the second cryogenic purifier and then, after cooling and purifying, the air is sent to the cryochamber, while the air regenerates and cools in the cryogenic purifier. After the system operation is finished, it is regenerated with the valves open and the heaters turned on.

Furthermore, a method for preparing cryogenic air fed to the cryogenic chamber, described in patent specification PL 213499, according to the invention, is known, which consists in drying and cooling of the air. This method is characterized by the fact that the air is subjected to filtration, then it is dried in a rotary dryer and then compressed and passed through a evaporator of the antechamber of the cryogenic chamber where the air is initially cooled to a temperature of 0° C. to minus 60° C., then the air is passed through the evaporators of the cryogenic chamber where the air cools down to the set temperature of minus 100° C. to minus 160° C. The air is passed through two evaporators located in the cryogenic chamber. The air is compressed to a pressure of 0 to 40 millibars. The air is compressed to a variable pressure, whereby the air is compressed to a higher value with the antechamber or cabin door open, while the air is compressed to a lower value with the antechamber and cabin door closed.

The same specification also discloses a device for the preparation of cryogenic air fed to the cryogenic chamber, which, according to the invention, is characterized in that it consists of a set of filters connected to a rotary dryer and the outlet of the rotary dryer is connected to an inlet of a turbine with flow control, while the turbine outlet is connected, with a duct, to an evaporator of the cryogenic chamber antechamber, and the antechamber evaporator outlet duct is connected to an inlet of the cryogenic chamber evaporator while the evaporator outlet comprises an inlet of the cryogenic chamber. Each evaporator is made of two sets of tubes, air and nitrogen, located next to each other. The air tubes are arranged between the nitrogen tubes and connected to them by cooling lamellas.

The disadvantages of the current solutions are the losses of liquid nitrogen that occur when it is fed during cryotherapy, the need to use quite extensive equipment in the form of heat exchangers, dryers, cryogenic purifiers and other devices, which increases the cost of procedures, for example in the event when the replacement of frosted heat exchangers is required.

In the case of cryosaunas eliminating the above problems, the effectiveness of the procedure is reduced due to the fact that cryotherapy in such case does not cover the entire human body, because there is no cryostimulation in the area of the head, upper arms, chest and back. These areas contain the largest number of cold receptors, estimated at approx. 40% of approx. 120,000. The existing cryosaunas do not have the functionality of applying a cold stream into the abovementioned areas because administering a non-breathable gas mixture around the head results in a life-threatening condition.

The solution according to the invention eliminates these disadvantages by completely eliminating nitrogen losses, simplifying the infrastructure needed to prepare a cryotherapy procedure, providing cryostimulation of the entire body of the patient, i.e. including the area of the head, upper arms, chest and upper back.

SUMMARY

The aim of the invention is also to prepare the air directed to the cryogenic chamber and cryosauna during the cryotherapy procedure in such a way that it allows for safe and effective performance of the procedure.

Essential for the solution is the method of preparing cryogenic air for use in cryotherapy procedures, which uses liquid nitrogen and gaseous oxygen, characterized by the fact that the liquid nitrogen is fed from the cryogenic nitrogen tank via a cryogenic duct to the reactor, wherein simultaneously a gas containing oxygen in a concentration from 20% to 100% is fed from an oxygen source to the reactor, through a gas duct, then, in the reactor, the liquid nitrogen is evaporated using the gas and both these components are mixed together, forming a cold breathing mixture, cooled to a set temperature of minus 80° C. to minus 160° C., which is further fed through a cold duct terminated with an outlet to a cryochamber.

Preferably, the reactor is located directly in the cryochamber.

Preferably, the cold breathing mixture is fed through the cold duct to the feeder, wherein the cold breathing mixture passes through the outlets onto the head and shoulder girdle of a human located in a cryosauna.

Preferably, the lower part of the cryochamber is supplied with the liquid/gaseous nitrogen mixture fed from the cryogenic nitrogen tank via a second line of the cryogenic duct.

Preferably, the lower part of the cryosauna is supplied with the liquid/gaseous nitrogen mixture fed from the cryogenic nitrogen tank via a second line of the cryogenic duct.

Preferably, the oxygen source is an oxygen concentrator.

In order to better illustrate the invention, the drawing includes a diagram presenting the method of preparing cryogenic air for use in cryotherapy procedures.

DETAILED DESCRIPTION OF THE PREFERRED EMBODIMENTS

Figure 1:
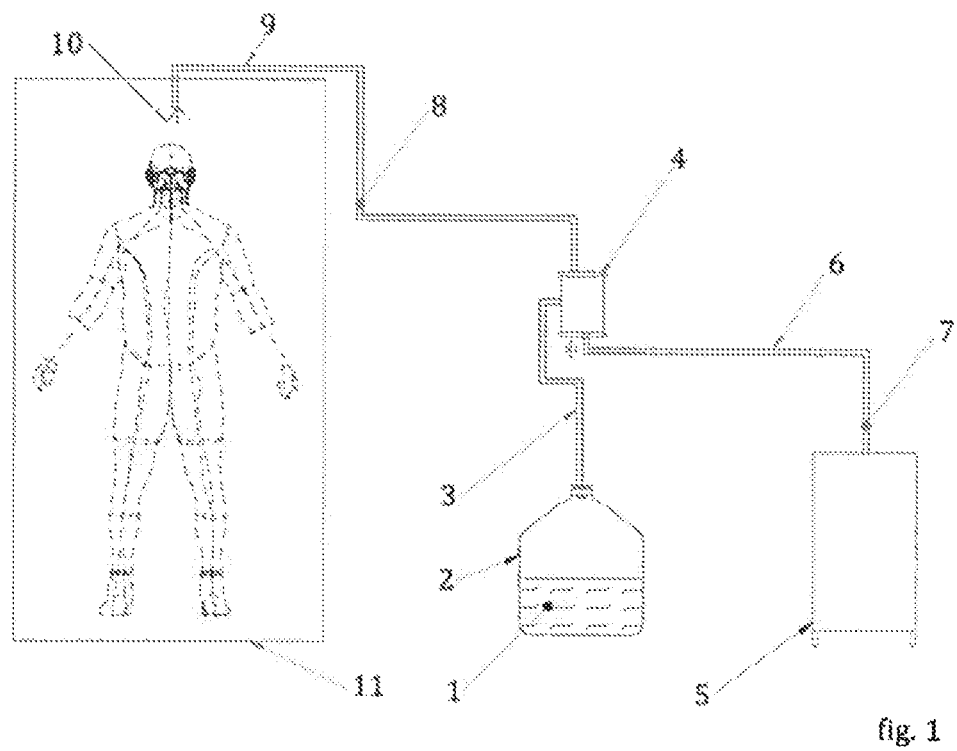
FIGS. 1 and 2 show the method of preparing cryogenic air, wherein such air is fed to the cryochamber in which the patient is located.

As depicted in FIG. 1, liquid nitrogen 1 is contained in a cryogenic nitrogen tank 2. Liquid nitrogen 1 is fed via a cryogenic duct 3 to a reactor 4. From an oxygen source 5, gas 7, which has an oxygen concentration of up to 100%, is fed to the reactor 4 via a gas duct 6. The reactor 4 is a device where the liquid nitrogen 1 is evaporated using the gas 7 and where the evaporated nitrogen is mixed with the gas with a high oxygen concentration. A cold breathing mixture 8 is formed, which is cooled to the set temperature of up to minus 160° C. It is then fed through a cold duct 9 terminated with an outlet 10 to a cryochamber 11.

Figure 2:
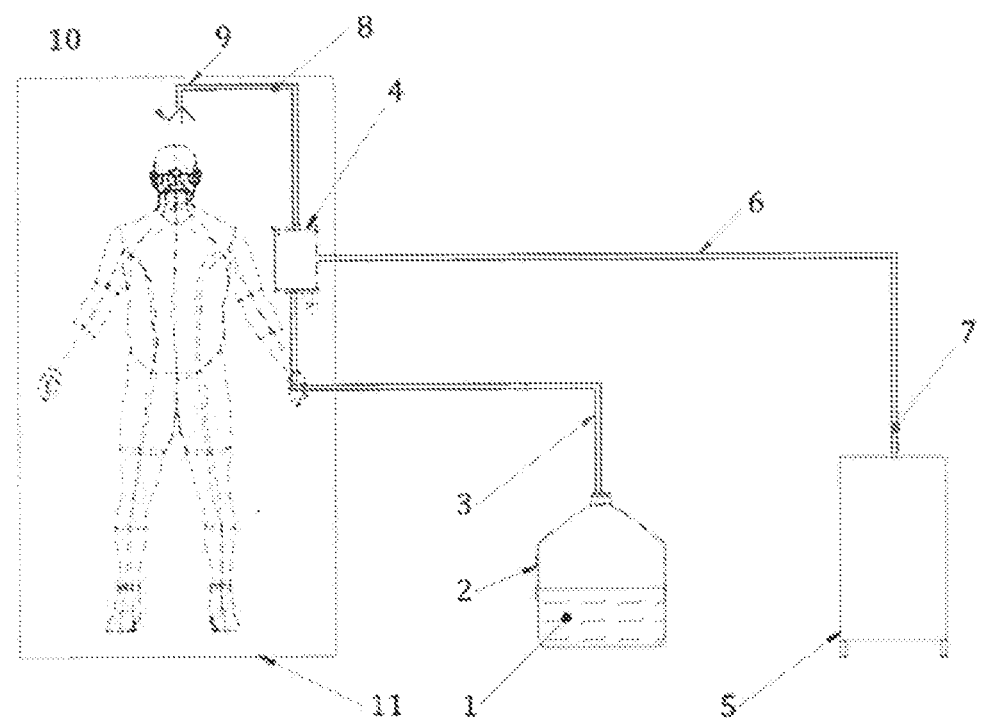

FIG. 2 presents a nitrogen tank 2, in which liquid nitrogen 1 is located, which is fed via a cryogenic duct 3 to a reactor 4, which is located in a cryochamber 11. Simultaneously, a gas 7 containing high concentration of oxygen is fed from an oxygen source 5 to the reactor 4 located inside the cryochamber, through a gas duct 6. In the reactor 4, the liquid nitrogen 1 is evaporated using the gas 7 and the evaporated nitrogen is mixed with oxygen. The indicated mixing process results in the formation of a cold breathing mixture 8 which is cooled to the set temperature of up to minus 160° C. The cold breathing mixture 8 is then fed through the cold duct 9 terminated with an outlet 10 to the cryochamber 11.

It is also possible to use the method according to the invention in existing cryosaunas where shoulder girdle and head were not subjected to cryotherapy treatment. This example is presented in FIG. 3. A nitrogen tank 2 contains liquid nitrogen 1, which is fed via a cryogenic duct 3 to a reactor 4. Meanwhile, a gas 7 containing high concentration of oxygen is fed from an oxygen source 5 to the reactor 4, through a gas duct 6. In the reactor 4, the liquid nitrogen 1 is evaporated using the gas 7 and the evaporated nitrogen is mixed with oxygen. With the mixing process, a cold breathing mixture 8 is created, which is cooled to a set temperature of up to minus 160° C. The cold breathing mixture 8 is then fed through a cold duct 9 to a feeder 12, and then it passes through the outlets 10 directly onto the head 14 and shoulder girdle 15 of a patient located in a cryosauna 13.

Figure 4:
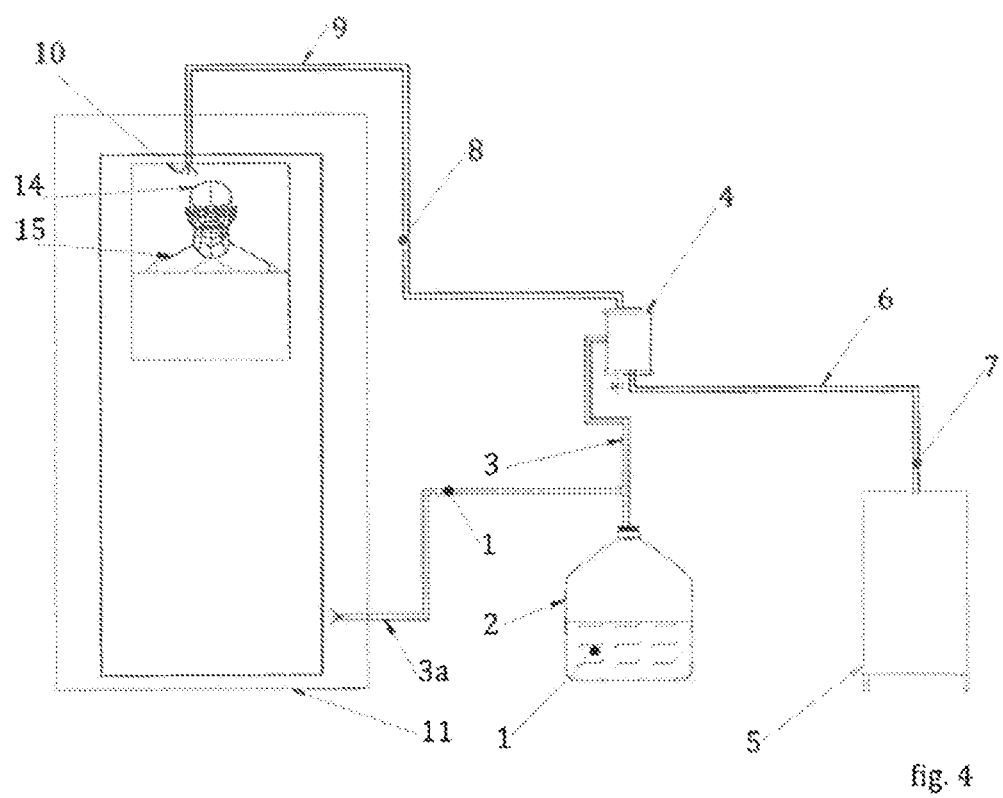
FIGS. 4 and 5 show the possibility of supplying the lower part of the cryochamber or cryosauna with the liquid/gaseous nitrogen mixture, and the upper part of the cryochamber or cryosauna with the breathing mixture.

FIG. 4 discloses a method of preparing cryogenic air, wherein the lower part of a cryochamber 11 is supplied with liquid nitrogen 1 fed directly from a cryogenic nitrogen tank 2, via a second line of the cryogenic duct 3a. Meanwhile in the reactor 4, the liquid nitrogen 1 is evaporated using a gas 7 and the evaporated nitrogen is mixed with oxygen. This creates a cold breathing mixture 8, which is cooled to the set temperature of up to minus 160° C., and then fed through a cold duct 9 terminated with an outlet 10 to a breathing part of a cryochamber 11.

Figure 5:
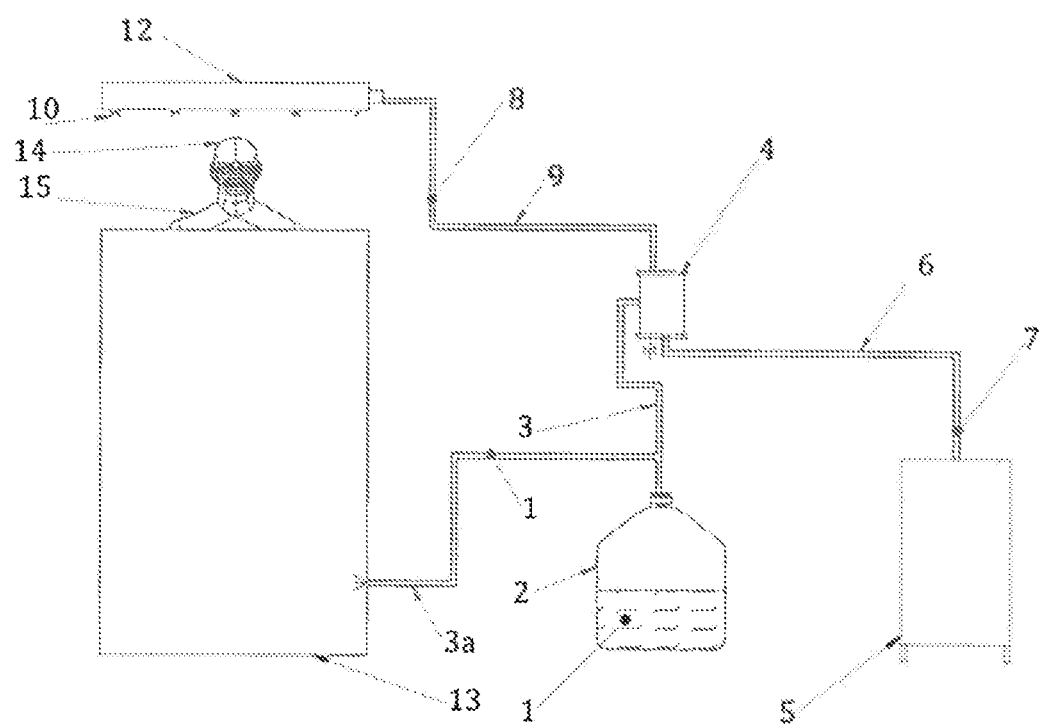

FIG. 5 shows, similarly to FIG. 4, the process of feeding the liquid/gaseous nitrogen mixture 1 directly from a cryogenic nitrogen tank 2 via a second line of the cryogenic duct 3a, but in this example this process takes place in a cryosauna 13. The nitrogen tank 2 contains liquid nitrogen 1, which is fed through the cryogenic duct 3 to the reactor 4. Meanwhile, a gas 7 containing high concentration of oxygen is fed from an oxygen source 5 to the reactor 4, through a gas duct 6. In the reactor 4, the liquid nitrogen 1 is evaporated using the gas 7 and the evaporated nitrogen is mixed with oxygen. With the mixing process, a cold breathing mixture 8 is created, which is cooled to a set temperature of up to minus 160° C. The cold breathing mixture 8 is then fed through a cold duct 9 to a feeder 12, and then it passes through the outlets 10 directly onto the head 14 and shoulder girdle 15 of a patient located in a cryosauna 13.

Apparatus for the preparation of cryogenic air, additionally a drain valve, which is designed to remove condensation and impurities formed during the operation of the reactor 4.

According to the method of preparing cryogenic air fed to the cryochamber, liquid nitrogen is evaporated in the reactor by a stream of oxygen gas with high oxygen content. As a result, the evaporated nitrogen mixes with oxygen to form a cold breathing mixture cooled to the set temperature. The cold breathing mixture is cryogenic air. After the delivery of cryogenic air to the cryochamber or cryosauna, in the first phase of exposure at very low temperatures, peripheral blood vessels and muscles contract, while the blood flow and metabolism slow down.

In the second phase, however, there is a defensive reaction involving a rapid expansion of blood vessels and an increase in blood flow. The result of this reaction is an increased supply of nutrients and oxygen, as well as anti-inflammatory mediators, to the cells. As a result, pain and inflammation are reduced, and damaged tissues regenerate faster. The muscles relax, metabolism accelerates, and the nervous and immune systems are stimulated.

For systemic cryotherapy, it is important that cryogenic air acts on receptors located in the area of the shoulder girdle (back, chest) and head. The invention allows the cooled gas to be blown directly onto the upper body. This significantly increases the effectiveness of the procedure as there is a stronger response of the patient's body to the effects of low temperature.

The invention provides the supply of cold air even in existing cryosaunas. The results of such cryotherapy are significantly better than in the case of known solutions.

The method according to the invention eliminates the loss of liquid nitrogen, which in turn significantly improves the efficiency of the entire process, and thus significantly reduces costs.

The reactor can be located next to the cryochamber and supply cryogenic air via a cold duct passing through an opening located in the cryochamber, or it can be located directly in the cryochamber.

Figure 3:
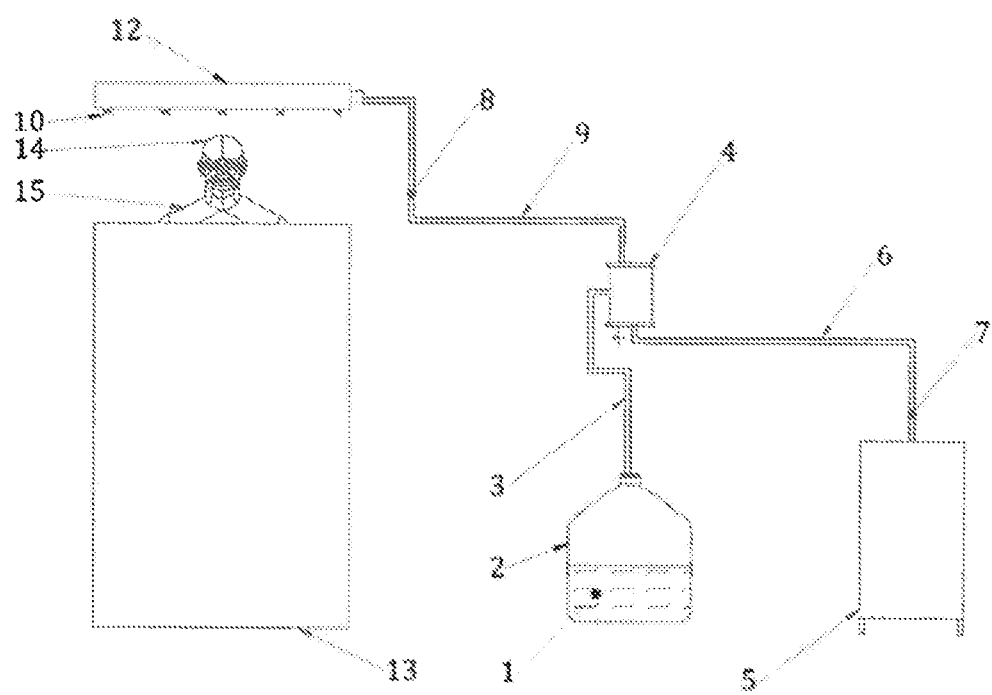
FIG. 3 shows the method of preparing cryogenic air, wherein the air is fed into an existing cryosauna, directly onto the patient's head and shoulder girdle.

As shown in the embodiments, the method of the invention can be both a completely separate cryotherapy system (FIGS. 1, 2 and 4), but it can also be an additional system that supplements an existing one, taking the form of an open cryosauna, over which the feeder with the outlet can be placed. This form is shown in FIG. 3 and FIG. 5, where the outlet and the feeder have outlets through which the cryogenic air is fed directly over people undergoing the cryotherapy process.

It is also possible to employ the method in commonly used cryosaunas, i.e. open chambers where the head and shoulder girdle are located above nitrogen vapors. Due to the fact that in cryosaunas the nitrogen gas zone is located close to the respiratory system, there is a danger of death if the person undergoing therapy faints and slips to the inside of the cryosauna. The use of the method according to the invention ensures a safe application of cold cryogenic air to the shoulder girdle and head.

In order to control the operation of the cryochamber or cryosauna, an interface is supplied on its wall or in its vicinity for controlling the device and monitoring all of its operating parameters.

The cryochamber is equipped with, among others, a temperature regulator that allows the temperature in the cabin to be adjusted at any time during the cryochamber operation. The current temperature in the cryochamber is presented on the control panel. In addition, the cryochamber has oxygen concentration control, procedure timer, microphone for communication with the patient during the procedure, and the ability to connect a music player via an appropriate connector. It also has a control for an emergency opening of the cryochamber door.

Cryochamber also allows to schedule the procedures. The cryochamber and cryosauna are to automatically turn on and start cooling in preparation for procedures scheduled for a specific date and time. It is also possible to repeat the scheduled treatments on specific days of the week, e.g. the chamber will be ready to work at 8 a.m. every day, except for the weekend.

The cryochamber is intended for whole-body cryotherapy, i.e. for carrying out the systemic cryotherapy procedures that include patient's head and shoulder girdle, i.e. areas where the most cold receptors are located.

The solution according to the invention is a cheaper and more efficient alternative to the systems used so far.

The method of preparing cryogenic air fed to the cryogenic chamber during cryogenic procedures may be used, among others, in health centers, spa facilities and sports clubs.

While the present invention has been described at some length and with some particularity with respect to the several described embodiments, it is not intended that is should be limited to any such particulars or embodiments or any particular embodiment, but it is to be construed with references to be appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

The invention claimed is:

1. A method of preparing cryogenic air for use in cryotherapy procedures, using liquid nitrogen and gaseous oxygen, comprising:
   feeding liquid nitrogen (1) from a cryogenic nitrogen tank (2) via a cryogenic duct (3) to a reactor (4),
   feeding simultaneously a gas (7) containing oxygen in a concentration from 20% to 100% from an oxygen source (5) to the reactor (4), through a gas duct (6),
   evaporating in the reactor (4) the liquid nitrogen (1) using the gas (7),
   mixing both these components together in the reactor (4), forming a cold breathable mixture (8),
   cooling the mixture (8) to a set temperature of minus 80° C. to minus 160° C.,
   feeding the mixture (8) through a cold duct (9) terminated with an outlet (10) to a cryochamber (11), wherein the method eliminates nitrogen losses during the cryotherapy procedure, and wherein the cryochamber has an oxygen concentration control.

2. The method of preparing cryogenic air according to claim 1, wherein the reactor (4) is located directly in the cryochamber (11).

3. The method of preparing cryogenic air according to claim 1, wherein the cold breathable mixture (8) is fed through the cold duct (9) to a feeder (12), wherein the cold breathable mixture (8) passes through outlets (10) onto a head (14) and shoulders (15) of a human located in a cryosauna 13.

4. The method of preparing cryogenic air according to claim 1, wherein the lower part of the cryochamber (11) is supplied with the liquid/gaseous nitrogen mixture (1) fed directly from the cryogenic nitrogen tank (2) via a second line of the cryogenic duct (3a).

5. The method of preparing cryogenic air according to claim 3, wherein the lower part of the cryosauna (13) is supplied with the liquid/gaseous nitrogen mixture (1) fed directly from the cryogenic nitrogen tank (2) via a second line of the cryogenic duct (3a).

6. The method of preparing cryogenic air according to claim 1, wherein the oxygen source (5) is an oxygen concentrator.

7. The method of preparing cryogenic air according to claim 1, wherein the cryochamber and cryosauna are automatically turn on and start cooling in preparation for the cryotherapy process according to a preset schedule, including scheduling of repeat treatments.

\* \* \* \* \*